United States Patent [19]

Yamamoto et al.

[11] 4,030,888
[45] June 21, 1977

[54] AUTOMATIC BLOOD ANALYZER

[75] Inventors: Hiroshi Yamamoto, Kobe; Masaaki Oka, Kakogawa, both of Japan

[73] Assignee: Toa Medical Electronics Co., Ltd., Kobe, Japan

[22] Filed: Feb. 17, 1976

[21] Appl. No.: 658,578

[30] Foreign Application Priority Data

Feb. 28, 1975 Japan ............................ 50-24531

[52] U.S. Cl. .................... 23/253 R; 23/230 B; 356/39; 356/40
[51] Int. Cl.² ..................................... G01N 33/16
[58] Field of Search ............ 23/253 R, 259, 230 B; 356/39, 40

[56] References Cited

UNITED STATES PATENTS

| | | | |
|---|---|---|---|
| 3,764,267 | 10/1973 | Farr ....................... | 356/40 |
| 3,861,877 | 1/1975 | Matharani et al. .............. | 23/253 X |
| 3,893,767 | 7/1975 | Fulwyler et al. ....................... | 356/39 |
| 3,901,658 | 8/1975 | Burtis et al. ....................... | 23/259 |
| 3,923,397 | 12/1975 | Shuck ....................... | 356/39 |
| 3,963,350 | 6/1976 | Watanabe et al. .................... | 356/39 |

*Primary Examiner*—R.E. Serwin
*Attorney, Agent, or Firm*—McNenny, Pearne, Gordon, Gail, Dickinson & Schiller

[57] ABSTRACT

A fully automatic system is disclosed for determining the seven blood parameters, red blood counts (RBC), hematocrit (HCT), white blood counts (WBC), mean corpuscular hemoglobin (MCH), mean corpuscular volume (MCV) and mean corpuscular hemoglobin concentration (MCHC). The blood sample collected is divided into two solutions, one for use in red blood counts and subjected to the colorimetric analysis for HGB determination and the other for use in white cell counts. A portion of the RBC solution is subjected to the double blood dilution and it enters a red cell counting portion. The peak value of electrical pulses supplied by said counting portion is indicative of the hematocrit. These data are used by preset arithmetic circuits to determine MCH, MCV and MCHC. White blood corpuscles are counted by a counting means of the same structure as that of the red cell counting portion. The flow of a diluent and the blood solution starting from the introduction of the sample, to counting portions, means for determination, and to the outlets are controlled by the supply of either vacuum or pneumatic pressure into two rotary proportioning cocks and chambers positioned upstream or downstream thereof.

4 Claims, 5 Drawing Figures

AUTOMATIC BLOOD ANALYZER

DETAILED DESCRIPTION OF THE INVENTION

This invention relates to a technique for automatically analyzing blood, and more particularly it relates to an automatic blood analyzing means which determines, counts and records seven parameters that are to be used for medical diagnosis of blood.

Most diagnoses in hospitals and physical examination centers are based on the results of several analyses performed by a variety of clinical analyzing means. But the principle of these analyzing means is in most cases an unsophisticated mechanization of analyses which have heretofore been conducted manually, and they perform only one function automatically. Nevertheless, in the wake of the recent development in electronics there is seen a greater possibility of reducing the scale of the present large and complicated apparatus and of carrying out a plurality of analyses simultaneously. The present invention reflects such recent trend in electronics.

The conventional method of blood analysis comprises counting under microscopic observation the number of red and white blood cells in a unit volume of blood, centrifuging the blood in a small tube to determine the hematocrit which is the proportion of red cells to a unit volume of blood, determining then the content of blood pigments (hemoglobin) in the unit volume, and finally, on the basis of the above red blood counts (RBC), hematocrit (HCT) and hemoglobin (HGB), obtaining the corpuscular constants that are used in actual diagnosis, i.e. mean corpuscular hemoglobin (MCH), mean corpuscular volume (MCV), and mean corpuscular hemoglobin concentration (MCHC). These constants can be formulated as follows:

a. MCH is an absolute mean value of hemoglobins in a red blood cell:

$$MCH\ (\mu\mu g) = \frac{HGB\ (g/dl) \times 10}{RBC\ (millions)}$$

b. MCV is an absolute mean value of the volume of a red blood cell:

$$MCV\ (\mu^3) = \frac{HCT\ (\%) \times 10}{RBC\ (millions)}$$

c. MCHC is an average concentration (%) of hemoglobins in a red cell:

$$MCHC\ (\%) = \frac{HGB\ (g/dl)}{HCT\ (\%)}$$

The white blood counts as well as the above corpuscular constants are used as data for analysis of blood.

Improved apparatuses that determined or counted these parameters were developed in recent years, and there was an advent of an analyzer which was able to process all of them simultaneously. But because of some problems found in detecting portions, the reliability of the analyzer was not necessarily higher than that of the conventional manual inspection method: examples of the problems are that one parameter was determined by use of more than one detecting portions or that the hematocrit determination was still effected by contrifuge or that one and the same hemolytic reagent was used to determine hemoglobin and leukocyte counts. In particular, if each parameter was determined by use of the conventional reagent and within the period of time that has been conventionally adopted, red cells or white cells were incompletely hemolyzed with the result that the determination of the parameter was inaccurate. Higher accuracy inevitably required a longer time of processing and determination, but then the rationale of automatization went for nothing. The use of one detector for determination of the two parameters, RBC and WBC, was always accompanied with clogging that added to the problems in maintenance of equipment. In addition, since WBC was counted a considerable time after hemolysis of red cells, reliability of the results of the determination was still doubtful.

What is more, the flow of fluids in the conventional apparatus was controlled by a number of electromagnetic valves which generated electrical noises, so that many additional components were necessary to eliminate these noises.

The conventional technique needed a relatively great amount of blood as a sample, so it was not applicable to infants, aged persons and other patients from whom much blood could not be drawn. In addition to this, cyanhemolytic reagents were suspected of causing environmental pollution and great care was necessary in handling them.

The present invention has been accomplished to eliminate the above mentioned defects of the conventional blood analyzer. In accordance with this invention, an accurate and reliable analysis can be rapidly performed by using only a minimum sample.

BRIEF DESCRIPTION OF THE DRAWINGS

Working examples of this invention are explained hereinafter with reference to the attached drawings wherein;

FIG. 1 is a basic flow chart of the fluid system. In hemoglobin determination, hemolytic reagents are used to destroy red blood corpuscles and liberate hemoglobin into the surrounding fluid. In this instance, the manual inspection method, which needs only a small amount of blood, advantageously uses the same sample to count white blood corpuscles. Since said hemolytic reagent destroys only red corpuscles and leaves white cells intact, hemoglobin is determined after white cell counts. However, the use of only one hemolytic reagent in an automatic analyzer makes it difficult to maintain the size of blood corpuscles during a predetermined time because the liquid sample is easily affected by the surrounding environment and temperature. Furthermore, extremely great errors may be caused because to prolong the reaction time or to set a desired time as in the case of the manual inspection technique is entirely impossible in the automatic method.

According to the means of the present invention, a liquid sample for determining hemoglobin and a liquid for white cells flow in two different channels, each employing a hemolytic reagent which differs from that used in the other, thereby enabling accurate and reliable determination and recording of every parameter under the optimal conditions of the sample (in the form of a solution). Other noticeable advantages of this invention are, for one thing, rapid processing of the sample due to independent hemolyses in different channels, and for another, constant analysis without the use of the pollutant, cyanhemolytic reagents.

Figure 1:
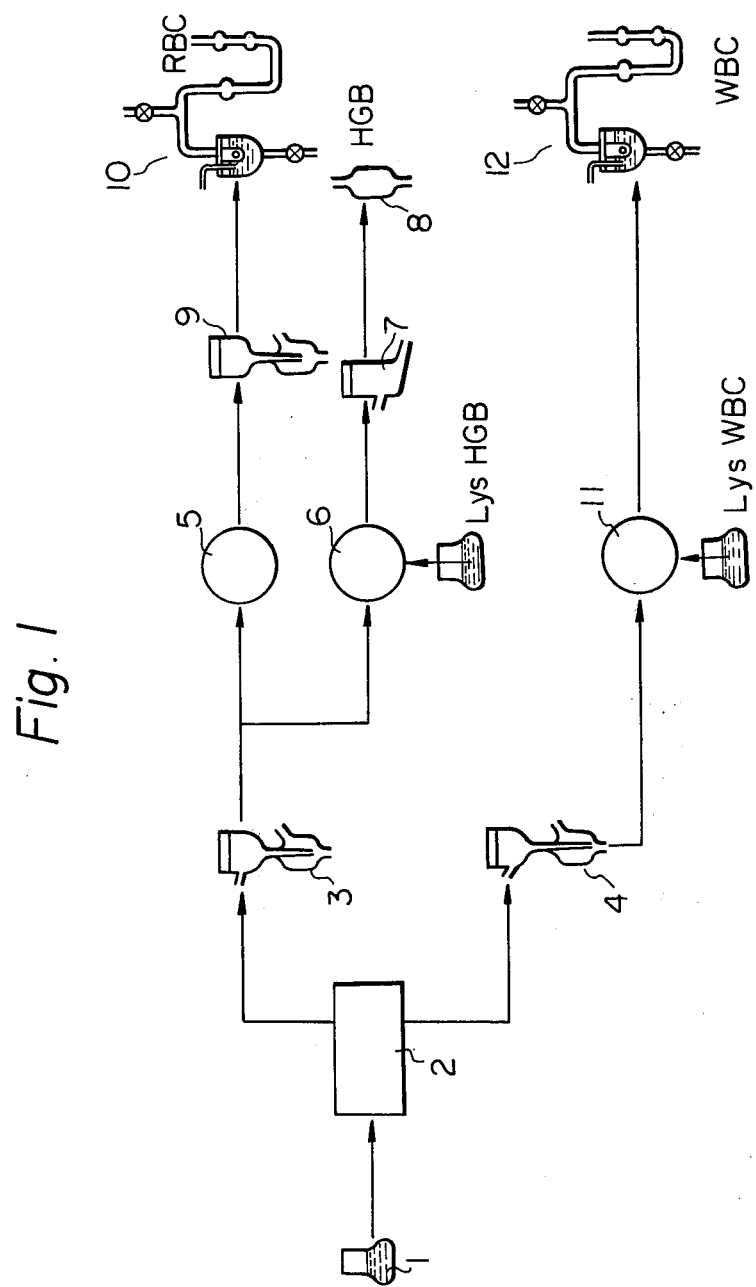
FIG. 1 is a basic flow chart of the fluid system.

In FIG. 1, a collected blood sample 1 is drawn by a proportioning cock 2 into chambers 3 and 4 where they are diluted and agitated with a diluent. A diluted sample in chamber 3 is used to count red cells and determine hemoglobin, and a diluted sample in chamber 4 is used to count white cells. A portion of the sample is drawn from the chamber 3 by a proportioning cock 5, and the remaining sample in said chamber is fed into a chamber 7 where it is agitated with a hemolytic reagent (used to determine hemoglobin only) that has been drawn by a proportioning cock 6, and finally sent to a cell in which the hemoglobin content is determined by colorimetric analysis.

On the other hand, the sample drawn by the proportioning cock 5 is sent to a chamber 9 where it is diluted and agitated with a diluent, and then at a red cell counting portion 10 operated by the same principle as that of the conventional corpuscle counter, the number of red cells is counted. The principle is to count electrical pulses which are generated when a solution in which corpuscles float enters an aperture which is disposed under the level of the solution and somewhat larger than corpuscles. In addition, by determining the amount of blood drawn in a U-shape tube that proportions a slight volume, corpuscles per unit volume of blood are counted. Since the peak value of each pulse is in a proportion to the size of a corpuscle, it is a measurement of the hematocrit.

A sample in the chamber 4 passes through a proportioning cock 11 which has drawn a given amount of a hemolytic reagent that is only used to count white cells; it is then fed into a leukocyte counting portion 12 similar to the erythrocyte counting portion 10.

Figure 2:
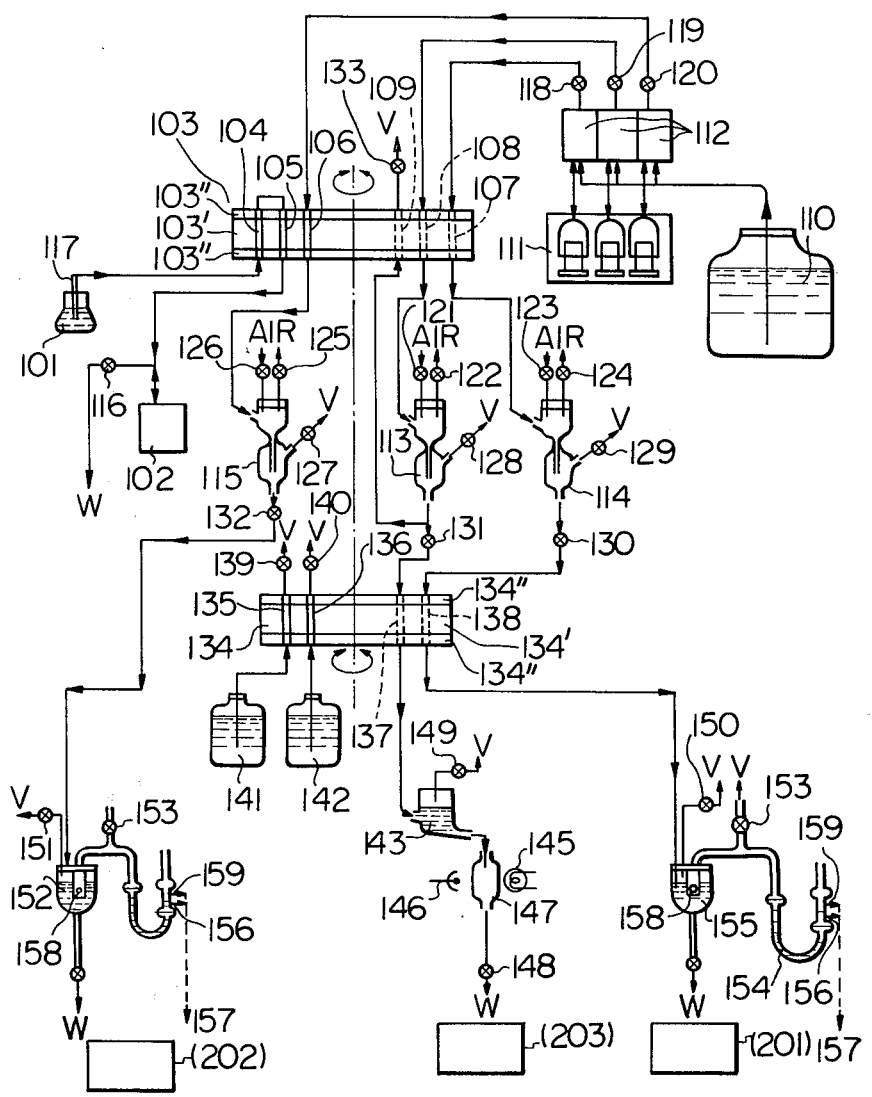
FIG. 2 is a more detailed diagram showing the flow of the fluid in FIG. 1.
Figure 3:
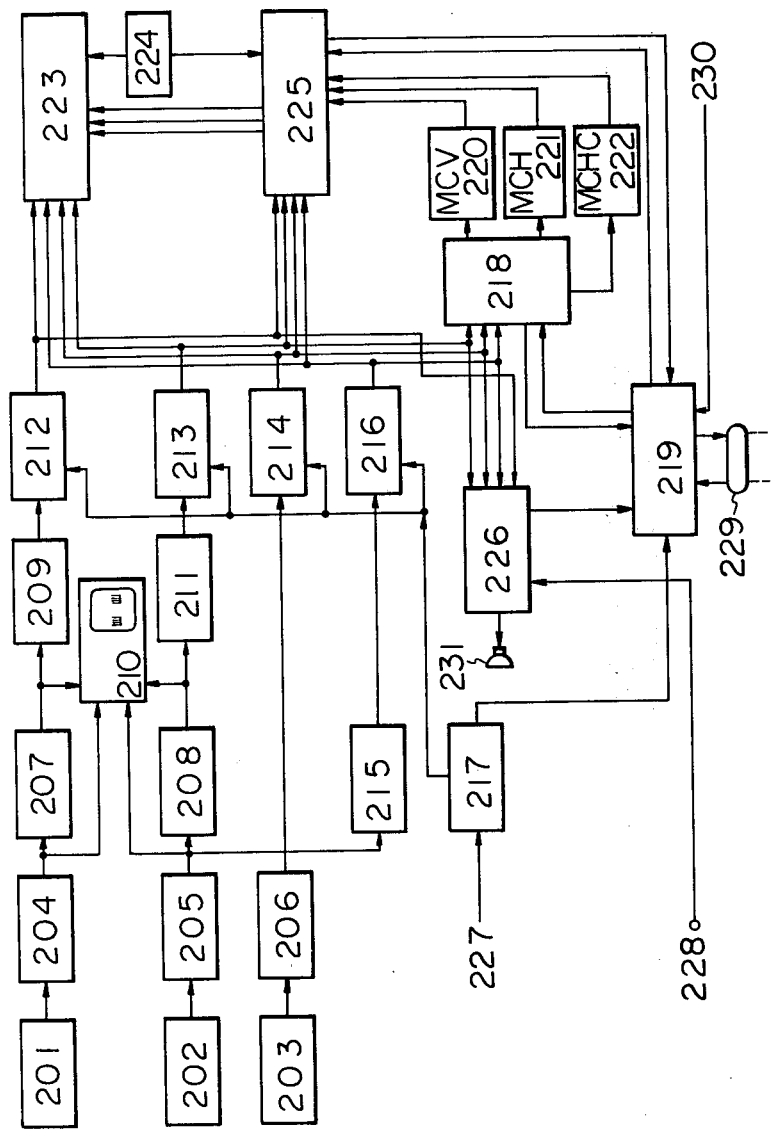
FIG. 3 is a block diagram showin one embodiment of an electrical circuit employed in accordance with the present invention.
Figure 4:
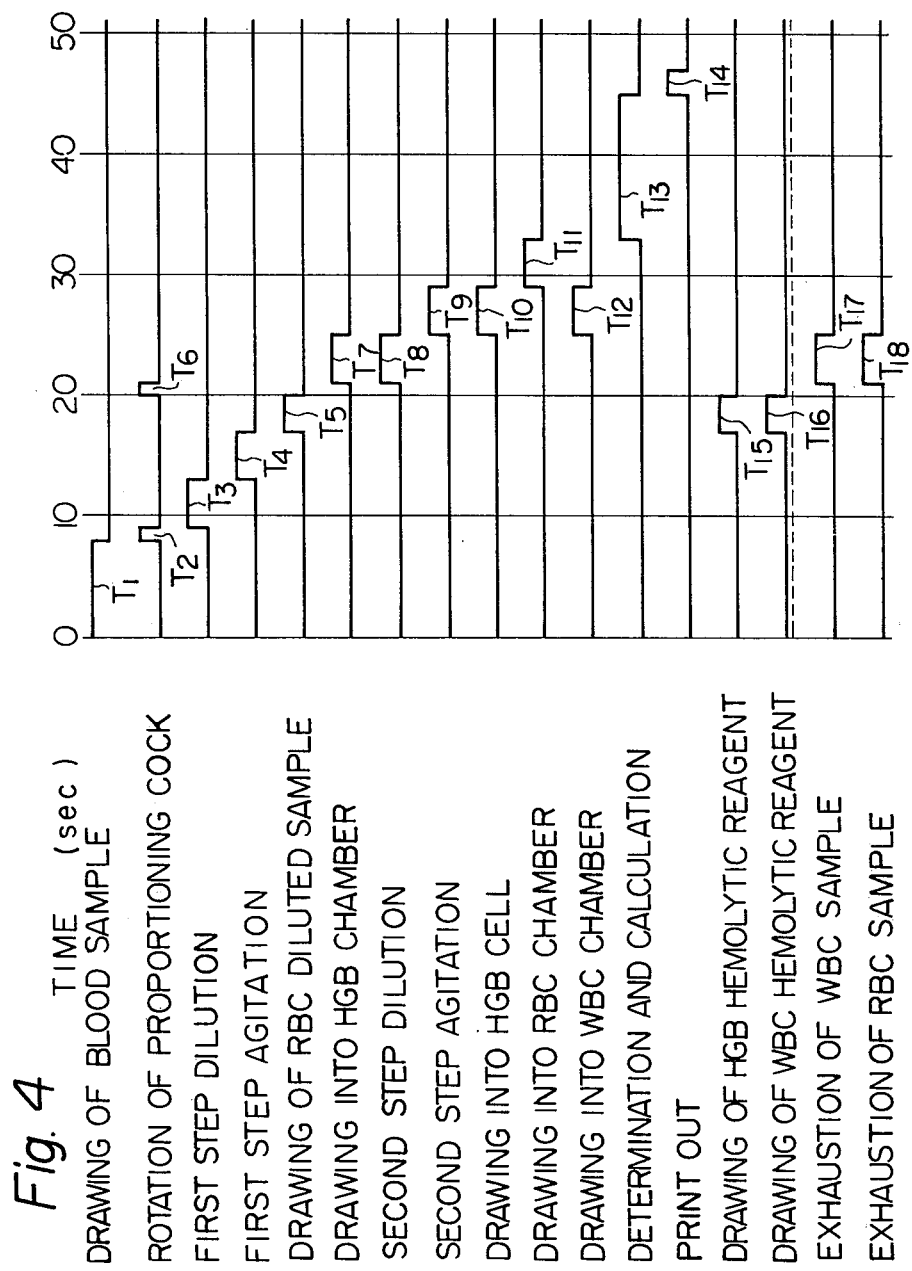
FIG. 4 is a time chart showing the operation of each component.

FIG. 2 is a more detailed diagram showing the flow of the fluid in FIG. 1. FIG. 3 is an electrical circuit which provides signals to operate the apparatus of the present invention. FIG. 4 is a time chart showing the operative mode of the apparatus described by FIGS. 2 and 3. According to FIG. 2 and 4, a blood sample 101 is sucked by a pump 102 and proportioned in passageways 104 and 105 of a proportioning cock 103, and waste blood is exhausted through a valve 116. The time chart of FIG. 4 suggests that the time $T_1$ required for sucking the initial blood is about 8 seconds. In this instance, a slight excess of blood is drawn so that all that remains after the previous processing is removed. The total amount of blood proportioned in the passageways 104 and 105 is 0.05 ml, but about 1.2 ml is preferably drawn in actual use in order to thoroughly wash the internal walls of the suction pipe 117 and the conduit connecting the two passageways.

In the next place, a member sandwiched between 103'' and 103''' is rotated halfway to shift the passageway 104 to the position of a passageway 107, and the passageway 105 to the position of a passageway 108. The time of rotation in this instance is represented by $T_2$.

A diluent 110 heated at about 37° C with a heat insulating means is drawn by a dilution pump 111 and proportioned in a diluent reservoir 112. The temperature is adjusted to the neighborhood of the temperature of the human body so that the swelling and constriction of corpuscles due to varying temperatures may not vary the hematocrit. The given amount of the diluent in the reservoir 112 is supplied to chambers 113 and 114 together with the blood sample proportioned in the cock 103. The diluent is forced out of valves 118 and 119. Valves 121 and 123 are opened to vent the chambers 113 and 114 to the atmosphere and air is supplied thereto even after the feeding of the diluent, thereby effecting constant agitation with air bubbles in the two chambers.

Figure 5:
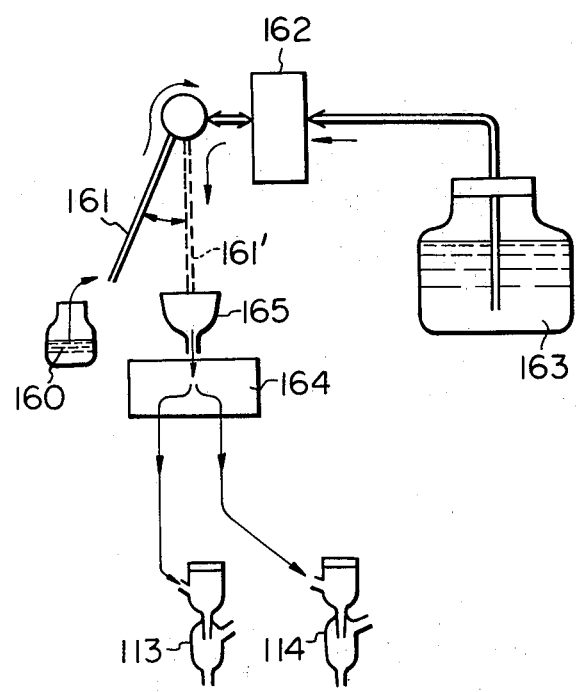
FIG. 5 shows apparatus for the drawing and dilution of blood in accordance with a further aspect of the present invention.

Drawing and dilution of blood may be effected in the manner described in FIG. 5 as a variation. This variation is advantageous in two respects: it requires an even smaller volume of blood, and the blood as it is introduced is not contaminated with foreign objects such as dust particles in the air. According to FIG. 5, about 0.05 ml of a blood sample is drawn by a suction and compression pump 162 and proportioned in a pipette 161. The pipette then shifts to the position 161' indicated by the broken line, and the pump 162 draws a given amount of a diluent 163 and forces it out in a receptacle 165 together with the blood sample. The internal walls of the pipette are thoroughly washed by the diluent. A flow splitter 164 splits the liquid mixture into proportioned amounts of two solutions, one for determining red cells and hemoglobin and the other for white cells, which are then sent to the chambers 113 and 114, respectively.

Turning now back to FIG. 2, when the valves 121 and 123 are closed while valves 122, 124 and valves 128, 129 are opened to suck the atmosphere, the diluted blood sample is transferred from the upper portion of the chambers 113 and 114 to the lower portion thereof, where agitation with air bubbles is effected as air is continuously drawn through valves 128 and 129. Chamber 113 is exclusively used for determination of RBC and HGB, and chamber 114 is for WBC. Upon completion of homogenization by dilution under agitation , a valve 133 connected to vacuum is opened thereby drawing a part of the solution in chamber 113 into passageway 109 of the proportioning cock 103. The time required for this drawing is represented by $T_5$ in FIG. 4. In the same manner as described in connection with the proportioning cock 103, a member 134' sandwiched between 134'' and 134''' of a proportioning cock 134 is rotated, and when valves 139 and 140 are opened simultaneously with valve 133, a hemolytic reagent 141 exclusively used for white cell counts and a hemolytic reagent 142 exclusively used for hemoglobin determination are drawn and proportioned in passageways 135 and 136 of the cock 134, respectively. The time required for this procedure is $T_{16}$ and $T_{15}$.

Subsequently, members 103' and 134' of the cocks 103 and 134 are rotated. The two cocks communicate with each other, and when liquids are drawn in the passageways (indicated by the solid line in FIG. 2) of the cock 103 and the passageways (indicated by the broken line) of cock 134, the other passageways indicated by the broken line of cock 103 as well as the passageways indicated by the solid line of cock 134 are empty, and vice versa upon halfway rotation of each cock. The time of rotation of each cock is indicated by $T_6$ (about one second).

Proportioning cock 103 thus returns to its initial position and it is ready for the suction of the next sample. It requires about 21 seconds to finish all the procedures above. If this flowing operation is continuously done, there is no interruption between the processing of one sample and next.

The solution for RBC which has been proportioned in the passageway 109 shifts to a passageway 106 upon rotation of the cock 103, when valve 120 is opened and said solution enters chamber 115 together with the diluent proportioned in the reservoir 112. This corresponds to the second step of the double dilution that has been conventionally effected by the manual inspection method, and the dilution under agitation in chamber 113 corresponds to the first step dilution. By the action of valves 125, 126 and 127, agitation and homogenization with air bubbles are effected in chamber 115 in the same fashion as in the first step mentioned before. The times required for second step dilution and agitation are $T_8$ and $T_9$.

At the same time, proportioning cock 134 is rotated, transferring the hemolytic reagents proportioned in passageways 135 and 136 to 138 and 137, respectively. By opening a valve 131, the diluted sample in chamber 113 enters a hemoglobin chamber 143 together with the hemolytic reagent in passageway 137. A valve 149 is then opened and agitation with air bubbles is performed in chamber 143. While agitation proceeds, red and white blood corpuscles are fully hemolyzed to convert hemoglobin to oxyhemoglobin, thus being enabled to carry out determination by colorimetric analysis. Time for drawing into the hemoglobin chamber is $T_7$. The sample is then sent to a cell 147 where the concentration of hemoglobin is determined by colorimetric analysis. The determination requires a time indicated by $T_{10}$. The cell is of the same construction as that of the commonly employed colorimeter; it comprises, for example, a light source 145 and a light receiver 146, using a light having a wavelength at 540 m$\mu$.

The hemolytic reagent (exclusively used to determine WBC) proportioned from reservoir 141 into passageway 138 of the cock 134 only hemolyzes red blood corpuscles completely and rapidly. This obviates the need of determining HGB using a liquid that remains after white cell counts. Not only that, white cell counts are performed more accurately without being influenced by the environment. When valves 130 and 150 are opened, the diluted sample in chamber 114 enters a white cell chamber 155 together with said hemolytic reagent in 138. The time required for this procedure is $T_{12}$.

On the other hand, valves 132 and 151 are opened, and the sample (for RBC) that has undergone the second step dilution in chamber 115 is forced into a red cell chamber 152. The time for drawing in this instance is indicated by $T_{11}$.

Subsequently, red cell determinations and counts are performed, on the basis of which final calculations are carried out, requiring a time represented by $T_{13}$. All six parameters are now available, and they are printed out and recorded in a printer. This takes a time indicated by $T_{14}$.

It takes the time indicated by $T_{17}$ to exhaust the WBC solution from chamber 155 while exhaustion of the RBC solution from chambers 147 and 152 requires the time represented by $T_{18}$. The time chart of FIG. 4 suggests that both exhaustion begins 21 seconds after the commencement of the drawing of the next blood sample.

The details of the portions where the blood corpuscles are counted are carried in our explanation of the block diagram of FIG. 1. We therefore refer to those portions just briefly: each of them comprises an aperture 158 below the surface of the solution, a valve 153, a U-shaped tube 154, a "start" electrode 156 and a "stop" electrode 159. Corresponding to a displacement of mercury in the tube 154, the solution enters the aperture 158. By counting corpuscles in the solution that passes through the aperture within a gate time defined by count start pulses which are generated upon passing of the mercury by the electrode 156 and count stop pulses generated upon passing of the same by the electrode 159, the number of corpuscles in a volume which corresponds to the volume of the tube defined by the two electrodes is obtained. p As mentioned before, the WBC counting portion and the RBC counting portion have the same construction.

In the following pages, we now describe the electrical circuit of the present invention in accordance with FIG. 4:

A white cell signal from a WBC detector 201 is amplified by an amplifier 204, separated from a noise signal by a peak discriminating circuit 207, and inputted into a count corrector circuit 209. The higher the concentration of corpuscles, the more corpuscles enter the aperture thus increasing the probability of two or more corpuscles passing through the aperture simultaneously or without interruption at all. Since this will still result in a single pulse even though two corpuscles are present in the aperture, errors due to such coincidence must be corrected. Corrected signals are counted by a WBC circuit 212.

A red cell signal from an RBC detector 202 is amplified by an amplifier 205, further processed by a discriminating circuit 208 and a count corrector circuit 211 (each having the same construction as that adopted in white cell counts), and enters an RBC circuit 213.

A monitor circuit 210 monitors the status of counting, and depending on the need, observes waveforms from each counting portion or checks any abnormal counts. It can also be used as an all-round oscilloscope to detect possible troubles and component malfunctions.

The mechanism of hemoglobin determination is as follows: an analog signal from a detector 203 is converted by an A-D convertor circuit 206 to pulses the number of which corresponds to the hemoglobin concentration, and said pulses are counted by a HGB counter circuit 214.

The hematocrit is determined in the following manner: a red cell signal provided from the RBC amplifier 205 is converted into a pulse signal by a convertor circuit 215 to provide the hematocrit by counting said pulse signal in a counter circuit 216.

The start and stop signal is supplied from a terminal 227 and controlled by a command signal from a start and stop controller circuit 217.

Signals from RBC circuit 213, HGB circuit 214 and HCT circuit 216 are inputted to a computation control circuit 218, and data and command signal necessary for calculation of the corpuscular constants are outputted to the following computation circuits, that is, MCV circuit 220, MCH circuit 221 and MCHC circuit 222.

An indicator member 223 indicates the results of determination and computation at each detecting portion as well as the indication of the number designated to each sample. A data recorder 225 also records the results of the analysis. A command for filling out other necessary information such as the date of determination is provided by an external switch 224.

The control of the entire system is centralized by a central control circuit 219 which receives signals from the components such as a start switch 230 and feeds a command thereto. The transmission and reception of signals between the central control circuit 219 and the fluid system are effected by way of a terminal 229.

An abnormality alarm circuit 226 monitors all portions where determinations are made, and if it detects any abnormality, it has an alarm speaker 231 provide an alarm and at the same time, transmits an abnormality signal to the control circuit 219 to discontinue determinations and recordings until an alarm clearing signal is provided through a terminal 228.

The fluid system is controlled by a fluid digital circuit (not shown) wherein valves are operated by pneumatic pressure. This control system is advantageous over the control by relaying in electrical circuit or the control by electromagnetic valves in that it is free from the fear of disturbance due to electrical noises and that it increases the reliability as well as durability of the apparatus.

As compared with the conventional blood analyzer that required a long time and a relatively great amount of blood samples and which could not analyze many samples in a short time without resulting in inaccurate determinations, the analyzing means of the present invention eliminates such defects and accomplishes automatic analysis of blood with high efficiency and great accuracy. It is therefore believed that contribution of this invention to diagnosis in medical fields is incalculable.

FIG. 1 shows the basic structure of the automatic blood analyzing means of the present invention. FIG. 2 is a detailed diagram of FIG. 1 and shows the flow of the fluid. FIG. 3 is a block diagram showing one embodiment of the electrical circuit employed in the means of the present invention. FIG. 4 is the time chart showing the operation of each component of said means. FIG. 5 is a variation of the component wherein blood is introduced.

Specific components of the means are as follows:
104, 108, 105 and 109 are proportioning means; 110 is a diluent; 113 and 114 are chambers where the first step dilution is effected under agitation; 111 and 112 are means for feeding the above chambers; 121, 122, 123 and 124 are means for agitation and homogenization; 141 is a WBC hemolytic reagent; 155 is a means for floating white cells; 158, 201 and 212 are means for counting white cells; 103 and 109 are means for proportioning part of RBC solution; 106 and 120 are means for the second step dilution; 115, 125 and 126 are means for homogenization under agitation; 152 is a means for counting red cells; 142 is a HGB hemolytic reagent; 143 is a means for converting hemoglobin to oxyhemoglobin; 145, 146, 147 and 214 are means for HGB determination; 215 and 216 are means for counting red cell pulses as a measurement of the hematocrit; 218 and 221 are MCH calculating means; 218 and 220 are MCV calculating means; and 218 and 222 are MCHC calculating means.

We claim:
1. In a system of automatic blood analysis for measuring white blood counts, red blood counts, hemoglobin and hematocrit of whole blood incorporating dilution, addition of reagents, agitation, mixing, corpuscular counting and hemoglobin determination, the combination which comprises means for determining white cell counts in a first flow channel and hemoglobin in a second flow channel with single blood dilution, and means for subjecting a portion of a sample in the flow channel for determining hemoglobin to a double blood dilution thereby enabling determination of red cell counts and the hematocrit.

2. A means for automatic analysis of blood which comprises a two-channel means for collecting proportioned amounts of blood, means for receiving blood in one of the channels of said collecting means and transferring the same together with a given amount of a diluent into a first chamber of a first step dilution where dilution under agitation is effected, means for agitating and homogenizing said diluent and the blood in said first chamber, means for adding to said diluted and agitated solution a given amount of a hemolytic reagent which is exclusively used for white cell counts thereby floating only white cells in said solution, means for counting white cells floating in said solution, means for receiving blood in the other channel of said collecting means and transferring the same together with a given amount of diluent into a second chamber of said first step dilution where dilution under agitation is effected, means for agitating and homogenizing said diluent and the blood in said second chamber, means for collecting a given amount of a portion of said diluted and agitated solution, a second step dilution means for diluting the thus proportioned solution to a higher dilution titer, means for agitating and homogenizing effected, means for agitating and homogenizing said diluent and the blood in said first chamber, means for adding to said diluted and agitated solution a given amount of a hemolytic reagent which is exclusively used for white cell counts thereby floating only white cells in said solution, means for counting white cells floating in said solution, means for receiving blood in the other channel of said collecting means and transferring the same together with a given amount of a diluent into the second chamber of said first step dilution where dilution under agitation is effected, means for agitating and homogenizing said diluent and the blood in said second chamber, means for collecting a given amount of a portion of said diluted and agitated solution, a second step dilution means for diluting the thus proportioned solution to a higher dilution titer, means for agitating and homogenizing the solution of said higher dilution, means for counting red cells in the thus homogenized solution, means for adding a hemolytic reagent exclusively used for hemoglobin determination to the solution that remains after proportioning of said given amount from said other channel thereby enabling the hemoglobin determination, and means for determining by colorimetric analysis the hemoglobin concentration in the thus obtained solution, means for converting red cell signal pulses provided by said red cell determination means to the hematocrit, means for calculating the mean corpuscular hemoglobin on the basis of the electrical hemoglobin signal from said colorimetric analyzing means for determining the hemoglobin concentration and the electrical hematocrit signal from said hematocrit convertor means, means for calculating the mean corpuscular the solution of said higher dilution, means including red cell counting means for counting red cells in the thus homogenized solution, means for adding a hemolytic reagent exclusively used for hemoglobin determination to the solution that remains after proportioning of said given amount from said other channel thereby enabling the hemoglobin determination, and means including colorimetric analyzing means for determining by colorimetric analysis the hemoglobin concentration in the thus obtained solution.

3. A means for automatic analysis of blood according to claim 2 including hematocrit convertor means for converting red cell signal pulses provided by said red cell counting means to the hematocrit, means for calculating the mean corpuscular hemoglobin on the basis of an electrical hemoglobin signal from said colorimetric analyzing means and an electrical hematocrit signal from said hematocrit convertor means, means for calculating the mean corpuscular volume on the basis of the electrical red cell signal from said red cell counting means and the electrical hematocrit signal from said hematocrit convertor means, and means for calculating the mean corpuscular hemoglobin concentration on the basis of the elecrical hemoglobin signal from said colorimetric analyzing means and the electrical hematocrit signal from said hematocrit convertor means.

4. A means for automatic analysis of blood comprising a two-channel means for collecting proportioned amounts of blood, means for receiving blood in one of the channels of said collecting means and transferring the same together with a given amount of a diluent into the first chamber of the first step dilution where dilution under agitation is effected, means for agitating and homogenizing said diluent and the blood in said first chamber, means for adding to said diluted and agitated solution a given amount of a hemolytic reagent which is exclusively used for white cell counts thereby floating only white cells in said solution, means for counting white cells floating in said solution, means for receiving blood in the other channel of said collecting means and transferring the same together with a given amount of a diluent into the second chamber of said first step dilution where dilution under agitation is effected, means for agitating and homogenizing said diluent and the blood in said second chamber, means for collecting a given amount of a portion of said diluted and agitated solution, a second step dilution means for diluting the thus proportioned solution to a higher dilution titer, means for agitating and homogenizing the solution of said higher dilution, means for counting red cells in the thus homogenized solution, means for adding a hemolytic reagent exclusively used for hemoglobin determination to the solution that remains after proportioning of said given amount from said other channel thereby enabling the hemoglobin determination, and means for determining by colorimetric analysis the hemoglobin concentration in the thus obtained solution, means for converting red cell signal pulses provided by said red cell determination means to the hematocrit, means for calculating the mean corpuscular hemoglobin on the basis of the electrical hemoglobin signal from said colorimetric analyzing means for determining the hemoglobin concentration and the electrical hematocrit signal from said hematocrit convertor means, means for calculating the mean corpuscular volume on the basis of the electrical red cell signal from said red cell counting means and the electrical hematocrit signal from said hematocrit convertor means, and means for calculating the mean corpuscular hemoglobin concentration on the basis of the electrical hemoglobin signal from said hemoglobin determination means and the electrical hematocrit signal from said hematocrit convertor means.

* * * * *

UNITED STATES PATENT AND TRADEMARK OFFICE
CERTIFICATE OF CORRECTION

PATENT NO. : 4,030,888
DATED : June 21, 1977
INVENTOR(S) : Hiroshi Yamamoto, Kobe; Masaaki Oka, Kakogawa both of Japan It is certified that error appears in the above-identified patent and that said Letters Patent are hereby corrected as shown below:

Claim 2, line 32, cancel beginning with "effected, means" to and including "mean corpuscular" in line 65.

Signed and Sealed this

Seventeenth Day of January 1978

[SEAL]

Attest:

RUTH C. MASON
*Attesting Officer*

LUTRELLE F. PARKER
*Acting Commissioner of Patents and Trademarks*